US009615838B2

(12) United States Patent
Nino et al.

(10) Patent No.: US 9,615,838 B2
(45) Date of Patent: Apr. 11, 2017

(54) TROCAR DEVICE WITH DETACHABLE HANDLE AND ASSOCIATED METHODS

(71) Applicant: ECA Medical Instruments, Newbury Park, CA (US)

(72) Inventors: John Nino, Simi Valley, CA (US); David Ivinson, Camarillo, CA (US)

(73) Assignee: ECA Medical Instruments, Newbury Park, CA (US)

( * ) Notice: Subject to any disclaimer, the term of this patent is extended or adjusted under 35 U.S.C. 154(b) by 0 days.

(21) Appl. No.: 15/004,299

(22) Filed: Jan. 22, 2016

(65) Prior Publication Data

US 2016/0199073 A1    Jul. 14, 2016

Related U.S. Application Data

(63) Continuation of application No. PCT/US2015/011259, filed on Jan. 13, 2015.

(51) Int. Cl.

| | |
|---|---|
| *A61B 17/34* | (2006.01) |
| *A61B 17/17* | (2006.01) |
| *A61B 17/16* | (2006.01) |
| *A61B 17/00* | (2006.01) |
| *B25D 5/02* | (2006.01) |
| *B25D 5/00* | (2006.01) |

(Continued)

(52) U.S. Cl.
CPC ...... *A61B 17/1728* (2013.01); *A61B 17/1604* (2013.01); *A61B 17/1633* (2013.01); *A61B 17/34* (2013.01); *A61B 17/3403* (2013.01); *A61B 17/3472* (2013.01); *A61B 17/3494* (2013.01); *A61B 17/3496* (2013.01); *A61B 2017/0046* (2013.01); *A61B 2017/00473* (2013.01); *A61B 2017/00477* (2013.01); *A61B 2017/3405* (2013.01); *A61B 2017/3407* (2013.01); *B25D 5/00* (2013.01); *B25D 5/02* (2013.01); *B26F 1/32* (2013.01); *B26F 1/34* (2013.01)

(58) Field of Classification Search
CPC ........ A61B 2017/0046; A61B 17/1604; A61B 17/1633; A61B 17/1728; A61B 17/34; A61B 17/3403; A61B 2017/3405; A61B 2017/3407; A61B 17/3472; A61B 17/3494; A61B 17/3496; B25D 5/00; B25D 5/02; B26F 1/32; B26F 1/34
See application file for complete search history.

(56) References Cited

U.S. PATENT DOCUMENTS 2,338,765 A * 1/1944 Hartman ................. B23B 49/00
   408/112
5,843,001 A * 12/1998 Goldenberg ......... A61B 10/025
   403/292

(Continued)

OTHER PUBLICATIONS

International Search Report dated Sep. 18, 2015, issued in International patent application PCT/US2015/011259 filed Jan. 13, 2015.

*Primary Examiner* — Larry E Waggle, Jr.
(74) *Attorney, Agent, or Firm* — Baker & Hostetler LLP

(57) ABSTRACT

The present disclosure provides methods for forming or enlarging holes in bone tissue and methods for fixing medical plates to bodies. The present disclosure also provides for products produced by the methods of the present disclosure and for apparatuses used to perform the methods of the present disclosure.

16 Claims, 10 Drawing Sheets

(51) Int. Cl.
*B26F 1/32* (2006.01)
*B26F 1/34* (2006.01)

(56) References Cited

U.S. PATENT DOCUMENTS

| | | | |
|---|---|---|---|
| 5,904,699 | A | 5/1999 | Schwemberger et al. |
| 6,502,491 | B2 * | 1/2003 | Borowczak .......... B26D 7/1818 30/362 |
| 7,338,494 | B2 * | 3/2008 | Ryan ................... A61B 17/1604 606/79 |
| 7,367,960 | B2 | 5/2008 | Stellon et al. |
| 9,327,359 | B2 * | 5/2016 | Wotruba ................ B23G 5/06 |
| 2006/0200182 | A1 | 9/2006 | Prosek |
| 2007/0016237 | A1 | 1/2007 | Smith |
| 2014/0257302 | A1 | 9/2014 | Nino et al. |
| 2014/0336717 | A1 * | 11/2014 | Predick ................. A61B 17/56 606/86 R |

* cited by examiner

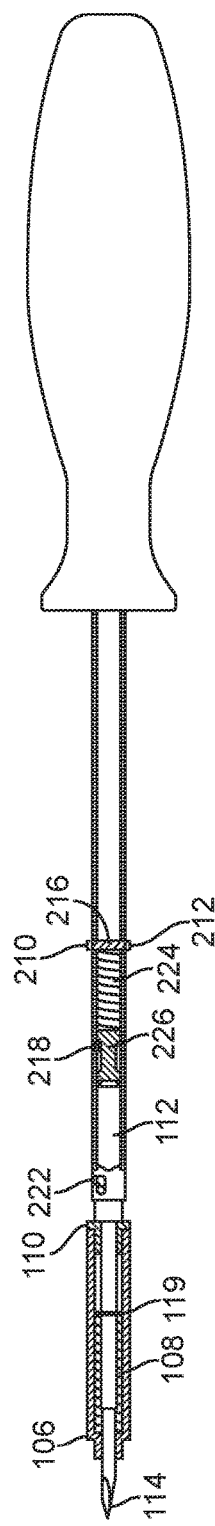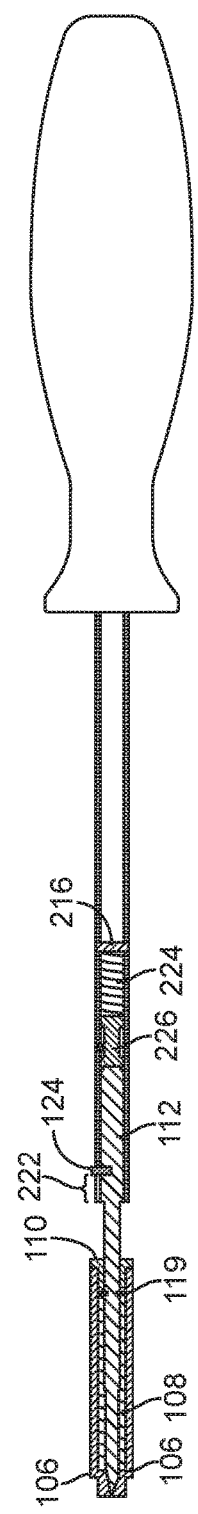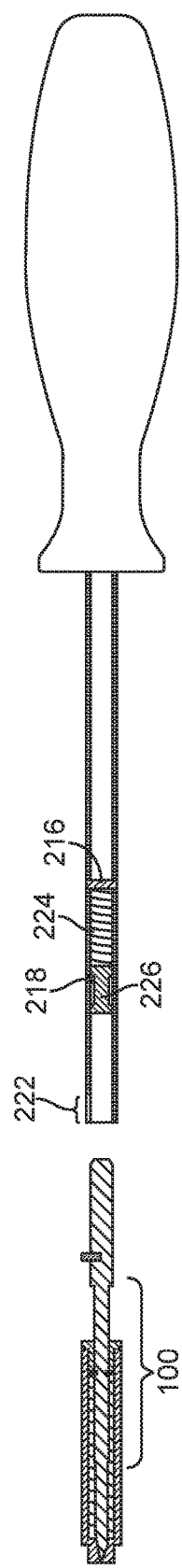

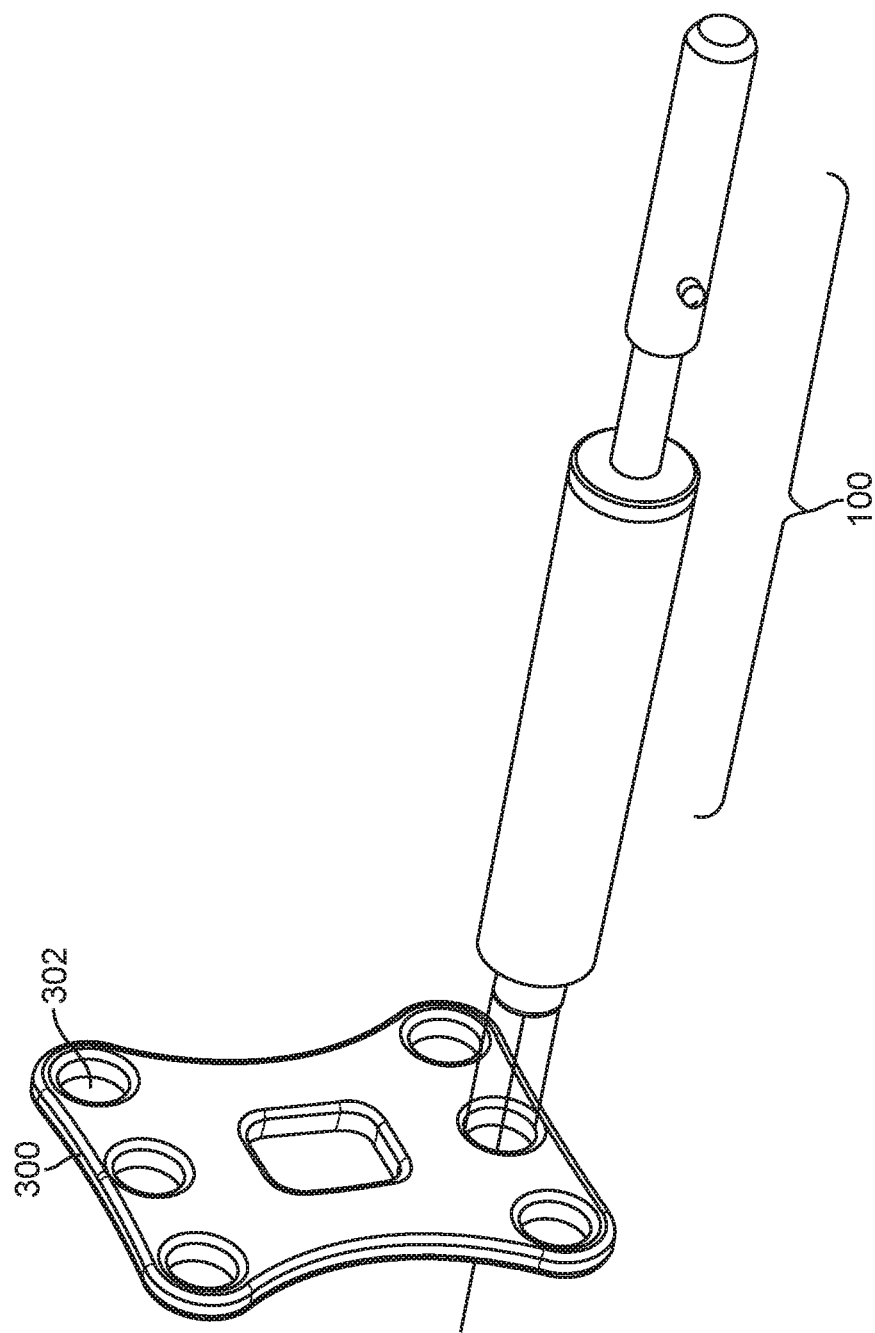

TROCAR DEVICE WITH DETACHABLE HANDLE AND ASSOCIATED METHODS

CROSS-REFERENCE TO RELATED APPLICATIONS

This patent application is a Continuation of international patent application PCT/US2015/011259 filed Jan. 13, 2015, the disclosure of which is incorporated by reference in its entirety.

FIELD OF THE DISCLOSURE

This disclosure is in the field medical treatment devices and methods. In particular, the disclosure relates to devices and methods for use in medical procedures including devices incorporating cutting tips for creating or enlarging holes in bone.

BACKGROUND

Orthopedic surgical procedures can require the creation or enlargement of holes in bones. In vertebral surgery, for example, precise alignment of holes is desirable, and in some instances alignment of holes is necessary for proper placement of medical devices, such as medical plates.

Thus, there is a need for medical devices that allow for precise alignment of holes in bone, including alignment of holes for use with other medical devices. The disclosure is directed to these and other important needs.

DISCLOSURE

The present disclosure provides aspects of trocar insertion systems comprising a driver handle with a driving shaft affixed thereto, a first mating feature on the end of the driving shaft opposite the driver handle, an elongated blade fixture having proximal and distal ends with a second mating feature on the distal end, a spring retention feature located on the elongated blade fixture between the proximal and distal ends, a collar feature located on the elongated blade fixture between the spring retention feature and the distal end, a spring housing cap slidably fitted around the elongated blade fixture between the spring retention feature and the collar feature, a trocar compression spring slidably fitted around the elongated blade fixture between proximal end and the spring retention feature, a spring housing comprising a hollow body with proximal and distal ends, wherein the distal end is fixedly attached to the spring housing cap, wherein the trocar compression spring and spring retention feature are enclosed within the interior volume of the spring housing, wherein the trocar compression spring is configured to be compressed between the spring retention feature and a spring catching feature located at the proximal end of the spring housing, and wherein at least a portion of the elongated blade fixture is slidably disposed within the spring housing with the central longitudinal axes of the elongated blade fixture and the spring housing being coaxially aligned, and wherein the first mating feature and second mating feature are detachably engaged such that the driving shaft and the elongated blade fixture are detachably connected in coaxial alignment.

The present disclosure provides kits comprising a driver handle with a driving shaft affixed thereto, wherein the driving shaft comprises a first mating feature on the end of the driving shaft opposite the driver handle, and one or more trocar assemblies, wherein each of the one or more trocar assemblies comprises an elongated blade fixture having proximal and distal ends with a second mating feature on the distal end, a spring retention feature located on the elongated blade fixture between the proximal and distal ends, a collar feature located on the elongated blade fixture between the spring retention feature and the distal end, a spring housing cap slidably fitted around the elongated blade fixture between the spring retention feature and the collar feature, a trocar compression spring slidably fitted around the elongated blade fixture between proximal end and the spring retention feature, and a spring housing comprising a hollow body with proximal and distal ends, wherein the distal end is fixedly attached to the spring housing cap, wherein the trocar compression spring and spring retention feature are enclosed within the interior volume of the spring housing, wherein the trocar compression spring is configured to be compressed between the spring retention feature and a spring catching feature located at the proximal end of the spring housing, wherein at least a portion of the elongated blade fixture is slidably disposed within the spring housing with the central longitudinal axes of the elongated blade fixture and the spring housing being coaxially aligned, and wherein the first mating feature and second mating features are configured for detachable engagement such that the driving shaft and the elongated blade fixture are detachably connected in coaxial alignment.

The present disclosure provides aspects of devices comprising an elongated blade fixture having proximal and distal ends with a mating feature on the distal end, a spring retention feature located on the elongated blade fixture between the proximal and distal ends, a collar feature located on the elongated blade fixture between the spring retention feature and the distal end, a spring housing cap slidably fitted around the elongated blade fixture between the spring retention feature and the collar feature, a trocar compression spring slidably fitted around the elongated blade fixture between proximal end and the spring retention feature, and a spring housing comprising a hollow body configured to slidably fit around the elongated blade fixture and attach to the spring housing cap.

The present disclosure provides methods of fixing a medical plate having one or more apertures to a body, the methods comprising positioning the medical plate adjacent to the body such that at least one of the one or more apertures is oriented towards the body, inserting a first trocar insertion system into a first one of the apertures oriented towards the body, wherein the first trocar insertion system comprises a driver handle with a driving shaft affixed thereto, a first mating feature on the end of the driving shaft opposite the driver handle, an elongated blade fixture having proximal and distal ends with a second mating feature on the distal end, a spring retention feature located on the elongated blade fixture between the proximal and distal ends, a collar feature located on the elongated blade fixture between the spring retention feature and the distal end, a spring housing cap slidably fitted around the elongated blade fixture between the spring retention feature and the collar feature, a trocar compression spring slidably fitted around the elongated blade fixture between proximal end and the spring retention feature, a spring housing comprising a hollow body with proximal and distal ends, wherein the distal end is fixedly attached to the spring housing cap, wherein the trocar compression spring and spring retention feature are enclosed within the interior volume of the spring housing, wherein the trocar compression spring is configured to be compressed between the spring retention feature and a spring catching feature located at the proximal end of the spring housing, wherein at least a portion of the elongated blade fixture is slidably disposed within the spring housing with the central longitudinal axes of the elongated blade fixture and the spring housing being coaxially aligned, and wherein the first mating feature and second mating feature are detachably engaged such that the driving shaft and the elongated blade fixture are detachably connected in coaxial alignment, the methods further comprising engaging the exterior of the first trocar insertion system spring housing with the first aperture oriented towards the body, applying a force to the driver handle relative to the medical plate to move the proximal end of the elongated blade fixture through the first aperture oriented towards the body, fixing the proximal end of the elongated blade fixture to the body, detaching the driving shaft from the elongated blade fixture by disengaging the first mating feature and second mating feature, and removing the driver handle with the driving shaft affixed thereto while leaving the proximal end of the elongated blade fixture fixed to the body.

The present disclosure provides methods of forming a pilot hole in bone tissue, the methods comprising positioning a medical plate having one or more apertures adjacent to the bone tissue such that at least one of the one or more apertures is oriented towards the bone tissue, inserting a first trocar insertion system into a first one of the apertures oriented towards the body, wherein the first trocar insertion system comprises a driver handle with a driving shaft affixed thereto, a first mating feature on the end of the driving shaft opposite the driver handle, an elongated blade fixture having proximal and distal ends with a second mating feature on the distal end, a spring retention feature located on the elongated blade fixture between the proximal and distal ends, a collar feature located on the elongated blade fixture between the spring retention feature and the distal end, a spring housing cap slidably fitted around the elongated blade fixture between the spring retention feature and the collar feature, a trocar compression spring slidably fitted around the elongated blade fixture between proximal end and the spring retention feature, a spring housing comprising a hollow body with proximal and distal ends, wherein the distal end is fixedly attached to the spring housing cap, wherein the trocar compression spring and spring retention feature are enclosed within the interior volume of the spring housing, wherein the trocar compression spring is configured to be compressed between the spring retention feature and a spring catching feature located at the proximal end of the spring housing, wherein at least a portion of the elongated blade fixture is slidably disposed within the spring housing with the central longitudinal axes of the elongated blade fixture and the spring housing being coaxially aligned, and wherein the first mating feature and second mating feature are detachably engaged such that the driving shaft and the elongated blade fixture are detachably connected in coaxial alignment, the methods further comprising engaging the exterior of the trocar insertion system spring housing with the aperture oriented towards the body, applying a force to the driver handle relative to the medical plate to move the proximal end of the elongated blade fixture through the aperture oriented towards the body, forming the pilot hole in the bone tissue with the proximal end of the elongated blade fixture, and removing the trocar insertion system from the medical plate aperture.

The general description and the following detailed description are exemplary and explanatory only and are not restrictive of the disclosure, as defined in the appended claims. Other aspects of the present disclosure will be apparent to those skilled in the art in view of the detailed description of the disclosure as provided herein.

DRAWINGS

The summary, as well as the following detailed description, is further understood when read in conjunction with the appended drawings. For the purpose of illustrating the disclosure, there are shown in the drawings exemplary implementations of the disclosure; however, the disclosure is not limited to the specific methods, compositions, and devices disclosed. In addition, the drawings are not necessarily drawn to scale. In the drawings.

Figure 8:
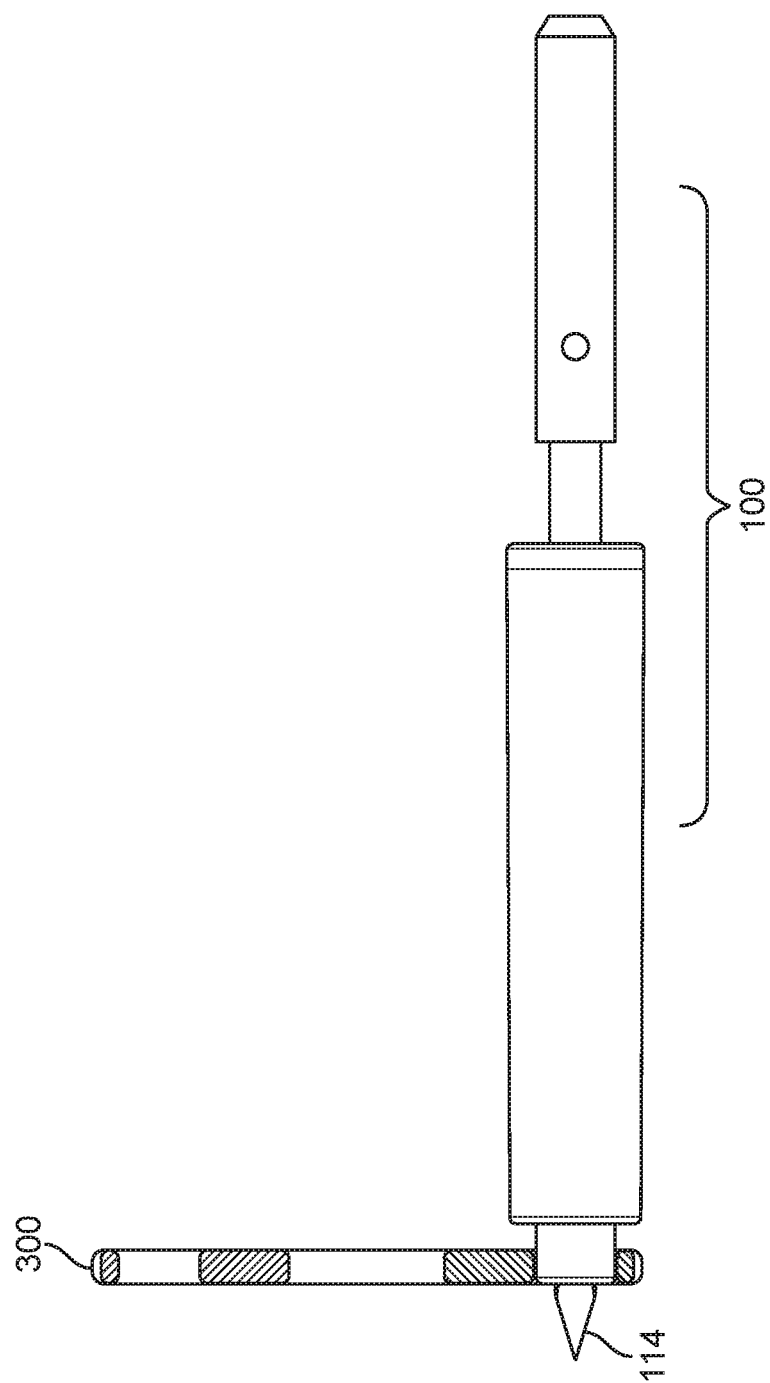
Figure 9:
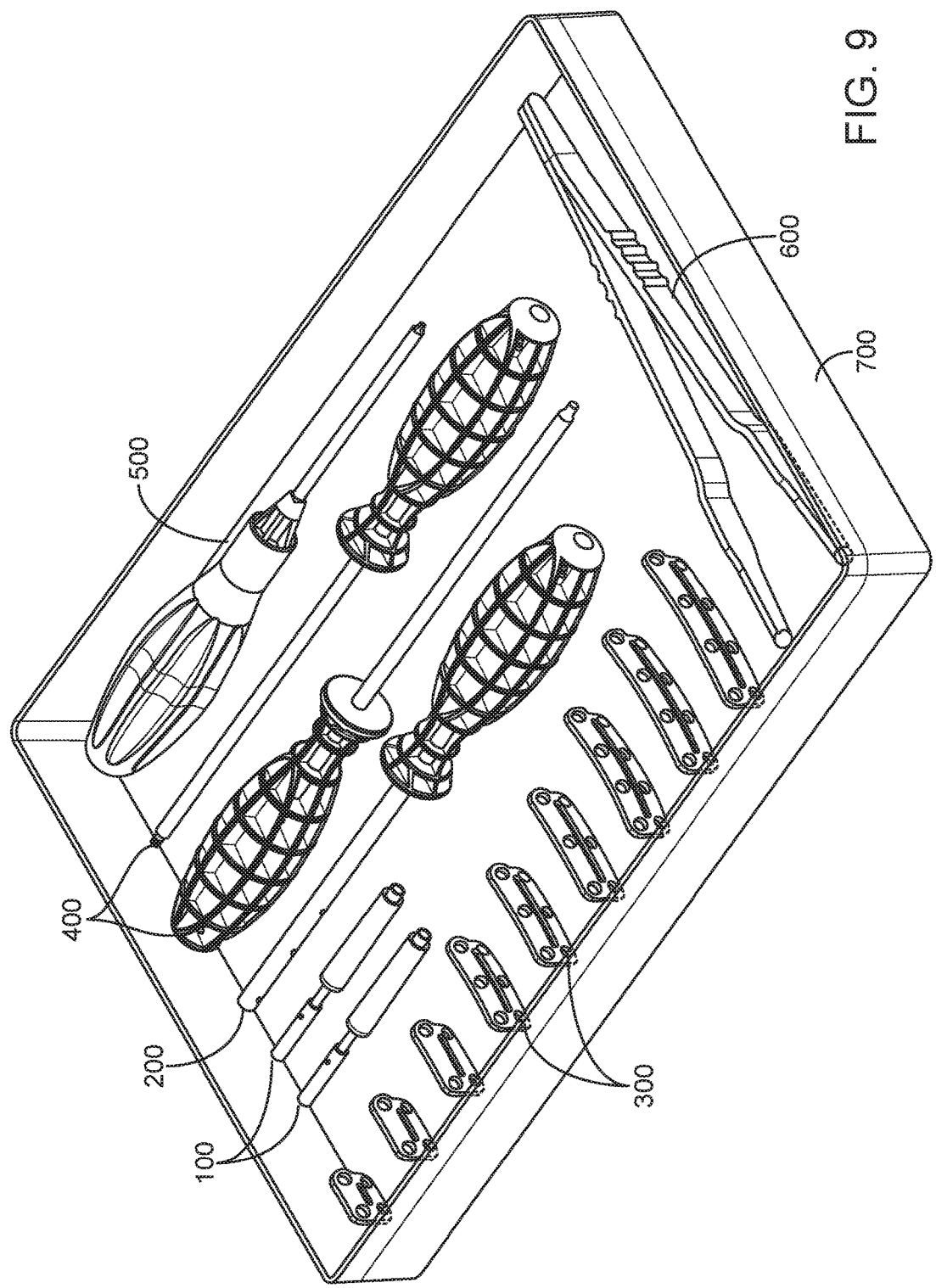

FIGS. 6A-C show cut-away views of aspects of a trocar insertion device;

FIGS. 7-8 illustrate aspects of a trocar insertion system;

FIG. 9 illustrates a trocar insertion system kit; and

Figure 10:
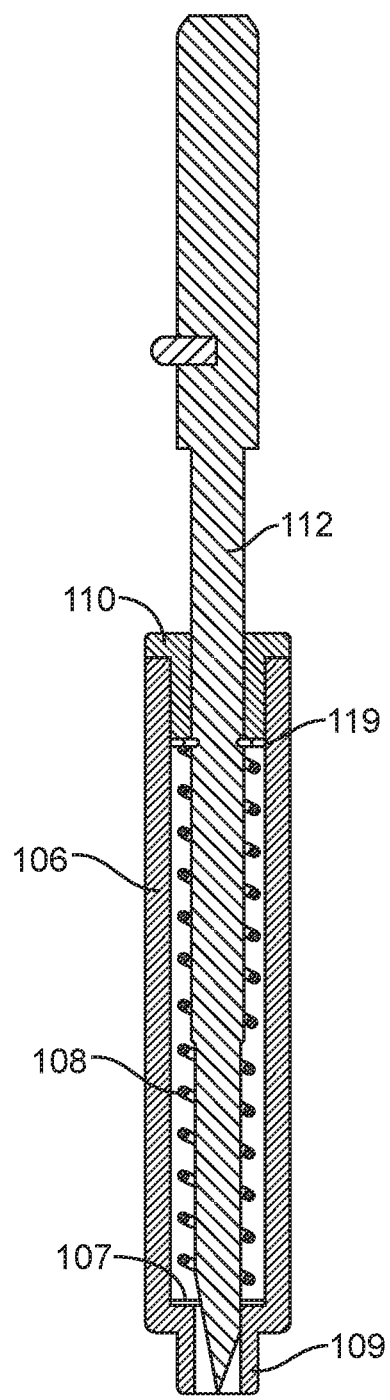

FIG. 10 shows a cut-away view of a portion of a trocar insertion device.

FURTHER DISCLOSURE

The present disclosure may be understood more readily by reference to the following detailed description taken in connection with the accompanying figures and examples, which form a part of this disclosure. It is to be understood that this disclosure is not limited to the specific devices, methods, applications, conditions or parameters described and/or shown herein, and that the terminology used herein is for the purpose of describing particular exemplars by way of example only and is not intended to be limiting of the claimed disclosure. Also, as used in the specification including the appended claims, the singular forms "a," "an," and "the" include the plural, and reference to a particular numerical value includes at least that particular value, unless the context clearly dictates otherwise. The term "plurality", as used herein, means more than one. When a range of values is expressed, another exemplar includes from the one particular value and/or to the other particular value. Similarly, when values are expressed as approximations, by use of the antecedent "about," it will be understood that the particular value forms another exemplar. All ranges are inclusive and combinable.

It is to be appreciated that certain features of the disclosure which are, for clarity, described herein in the context of separate exemplar, may also be provided in combination in a single exemplary implementation. Conversely, various features of the disclosure that are, for brevity, described in the context of a single exemplary implementation, may also be provided separately or in any subcombination. Further, reference to values stated in ranges include each and every value within that range.

Figure 1:
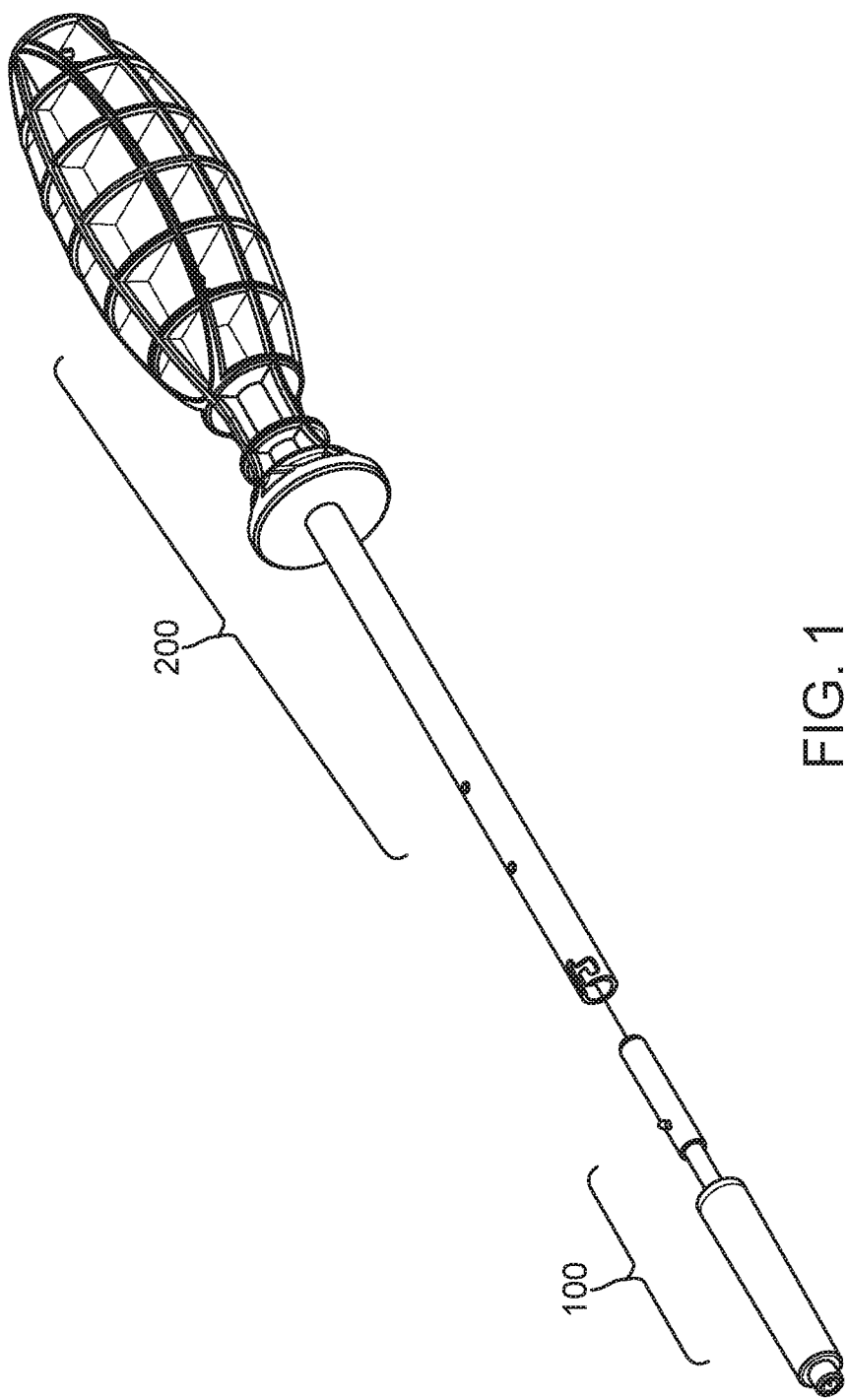
FIG. 1 illustrates aspects of a trocar insertion device.
Figure 2:
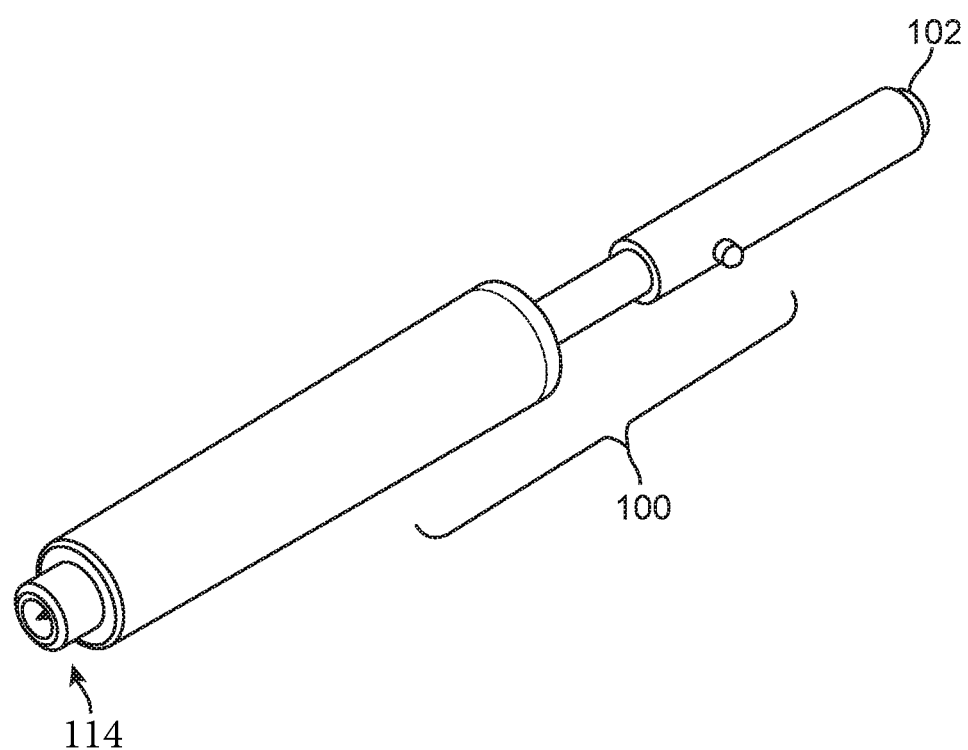
FIG. 2 illustrates aspects of a portion of a trocar insertion device.
Figure 3:
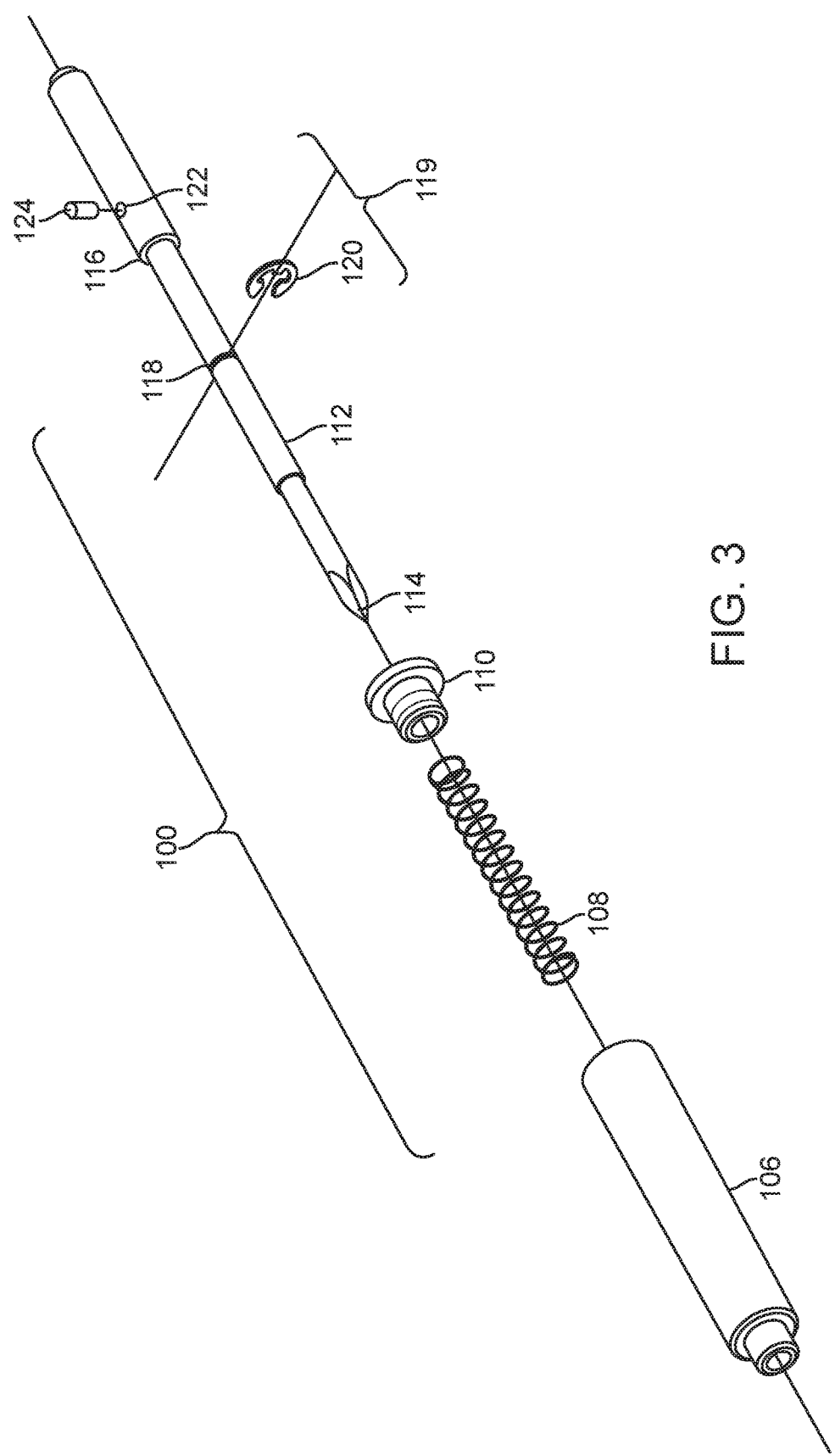
FIG. 3 illustrates an assembly view of aspects of a trocar insertion device.
Figure 4:
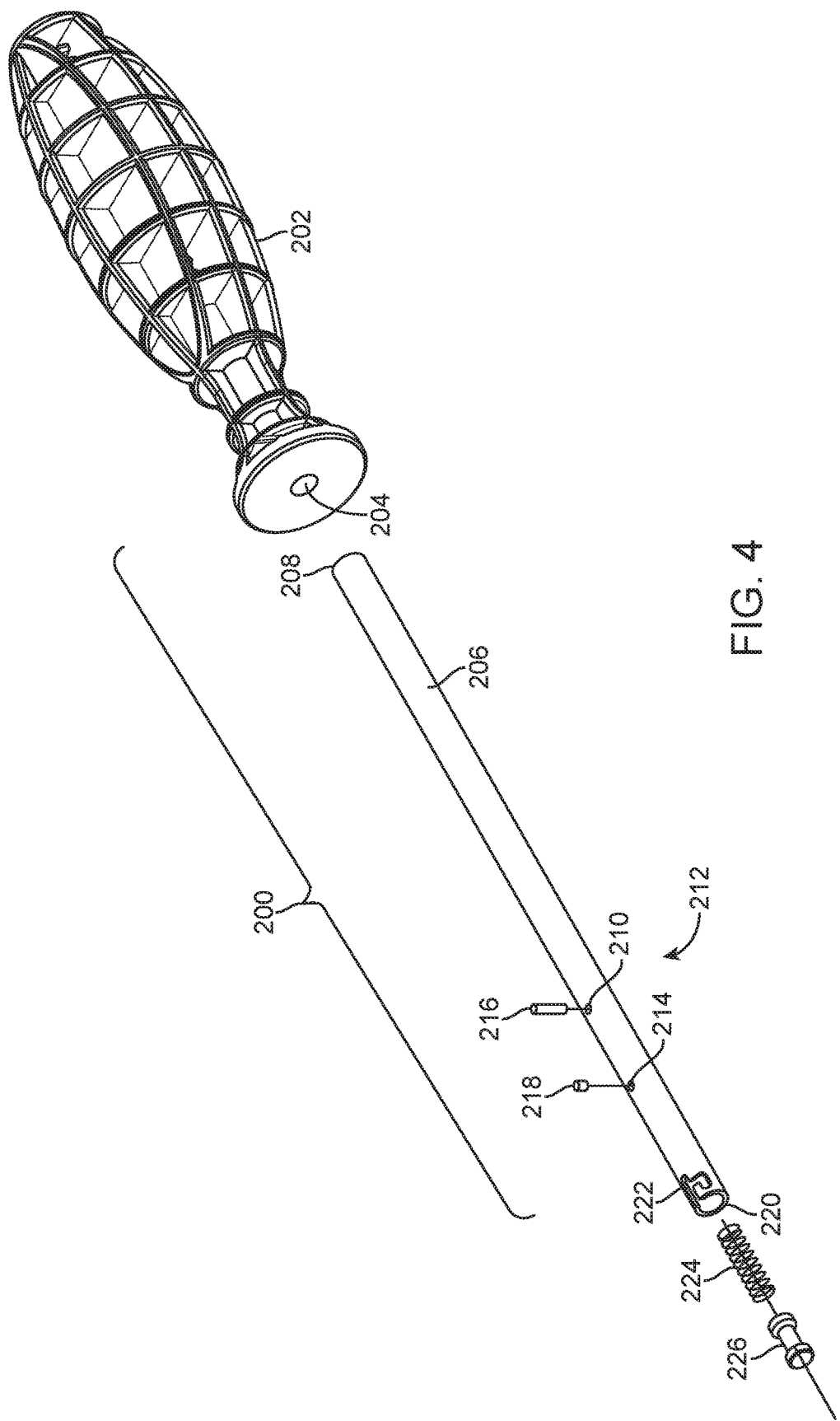
FIG. 4 illustrates an assembly view of aspects of a trocar insertion device.

In one aspect, the present disclosure provides trocar insertion systems. As depicted in FIG. 1, the trocar insertion system may comprise a trocar assembly 100, which can be detachably connected to a handle assembly 200 using mating features provided thereon. Exemplary implementations of the handle assemblies 200 and trocar assemblies 100 are depicted in FIGS. 3 and 4. In some exemplars, the trocar insertion systems may comprise a driver handle (202) with a driving shaft (206) affixed thereto, a first mating feature on the proximal end (220) of the driving shaft (206) opposite the driver handle (202), an elongated blade fixture (112) having a proximal end (114) and a distal end (102) with a second mating feature on the distal end, a spring retention feature (119) located on the elongated blade fixture (112) between the proximal and distal ends (114/102), a collar feature (116) located on the elongated blade fixture (112) between the spring retention feature (119) and the distal end (102), a spring housing cap (110) slidably fitted around the elongated blade fixture (112) between the spring retention feature (119) and the collar feature (116), a trocar compression spring (108) slidably fitted around the elongated blade fixture (112) between the proximal end (114) and the spring retention feature (119), a spring housing (106) comprising a hollow body with proximal and distal ends, wherein the distal end is fixedly attached to the spring housing cap (110), the trocar compression spring (108) and spring retention feature (119) are enclosed within the interior volume of the spring housing (106), the trocar compression spring (108) is configured to be compressed between the spring retention feature (119) and a spring catching feature (107) located at the proximal end of the spring housing (106), and at least a portion of the elongated blade fixture (112) is slidably disposed within the spring housing (106) with the central longitudinal axes of the elongated blade fixture (112) and the spring housing (106) being coaxially aligned. The first mating feature and second mating feature can be detachably engaged such that the driving shaft (206) and the elongated blade fixture (112) are detachably connected in coaxial alignment. The spring retention feature (119) may comprise any feature present on the elongated blade fixture (112) that is capable of retaining one end of a compression spring in a fixed position as the spring is compressed against the feature. In some instances the spring retention feature (119) comprises a retaining ring or clip (120) that is positioned within a slot or groove (118) on the elongated blade fixture (112). In some instances, self-locking retaining rings can be used without a slot or groove on the shaft of the elongated blade fixture. Driver handle (202) can be a suitable shape to be gripped in a human hand. In some instances, the driver handle can be a welled handle suitable for medical waste collection during use, as described in U.S. patent application Ser. No. 13/983,535. Driving shaft (206) can be affixed within driver handle (202) such that rotation of the driver handle (202) creates rotation of the driver shaft (206) with no slippage. In some instances, the distal end (208) of the driving shaft (206) is affixed within an aperture (204) of driver handle (202).

Spring housing (106) can be formed with any suitable external profile. A cylindrical cross-section is suitable for some applications, while other polygonal, star-shaped, keyed, flanged, or grooved cross-sections may be also suitable in other exemplary implementations. The proximal end (114) of the elongated blade fixture (112) can be located at the center of the cross-section of spring housing (106) or at other positions as desired, provided the proximal end (114) can slide through the end of spring housing (106) during operation.

The trocar assembly (100) and handle assembly (200) can be detachably connected using any suitable pair of first and second mating features that allow for connection and disconnection with coaxial alignment between the driving shaft (206) and elongated blade fixture (112). In some instances, the first mating feature and second mating feature comprise a pair of helical threads that can detachably engage together. In some instances, the first and second mating features comprise a ball detent mechanism arrangement wherein one of the driving shaft (206) and elongated blade fixture (112) can be received within the other such that a spring-loaded ball falls partially into an aperture in order to detachably connect the driving shaft (206) and elongated blade fixture (112). In some instances, the second mating feature comprises a protruding part and the first mating feature comprises a depression adapted to receive the protruding part in a snap joint configuration. Trocar assembly (100) can include an area suitable for grasping by a user, such as the area of the elongated blade fixture (112) between trocar locator pin (124) and spring housing cap (110). The grasping area can be configured for enhanced grip by methods known in the art including incorporating coated or textured surfaces, depressions, grooves, or cut-outs that allow for improved grasping and controlled twisting of the trocar assembly (100) as it is engaged with the handle assembly (200), provided the features do not interfere with the slidable engagement of the spring housing cap (110) and spring housing (106) around the elongated blade fixture (112) as trocar compression spring (108) is compressed.

In some exemplars, trocar assembly (100) and handle assembly (200) can be detachably connected with spring-loaded configurations. In some exemplars, the driving shaft (206) comprises a hollow tube with a first aperture (210) and a second aperture (212) through the walls of the hollow tube on opposite sides of the central longitudinal axis of the hollow tube, a third aperture (214) through the wall of the hollow tube in a position between the location of the first and second apertures and the proximal end of the hollow tube, and a groove (222) through the wall of the hollow tube at the proximal end. In the spring-loaded configurations, the trocar insertion systems further comprise a spring stop pin (216) fixed within the first and second apertures (210/212) and passing through the central longitudinal axis of the hollow tube, a control pin (218) fixed within the third aperture (214) and partially extending into the interior volume of the hollow tube, and a spring pressure pin (226) comprising a cylinder configured to slide within the interior of the hollow tube, positioned within the interior volume of the hollow tube with the longitudinal axis of the cylinder aligned with the hollow tube longitudinal axis. In the spring-loaded configurations the spring pressure pin (226) can have a reduced diameter in a portion of the middle of the side walls, the reduction in diameter can be at least as large as the portion of the control pin that partially extends into the interior volume of the hollow tube, and the spring pressure pin (226) can be positioned such that the portion of the control pin that partially extends into the interior volume of the hollow tube is slidably contained within the volume of the reduced diameter portion of the spring pressure pin (226) between the two non-reduced-diameter end regions of the spring pressure pin (226). In these instances, a handle compression spring (224) can be positioned within the interior volume of the hollow tube between the spring stop pin and the spring pressure pin (226), and a fourth aperture can be located on the elongated blade fixture (112) between the collar feature (116) and the distal end, the distal end of the elongated blade fixture can be configured to slidably fit within the interior of the proximal end of the hollow tube, a trocar locator pin (124) can be fixed within the fourth aperture (122) and partially extending outward from the elongated blade fixture (112) surface. For connection of the trocar assembly (100) to the handle assembly (200), the driving shaft (206) and elongated blade fixture (112) can be detachably connected by the detachable engagement of the trocar locator pin (124) within the groove (222) of the driving shaft (206), and the handle compression spring (224) can be at least partially compressed by the spring pressure pin (226), which can be slidably contained between the distal end of the elongated blade fixture (112) and the handle compression spring (224). Aspects of some exemplars of such engagement are depicted in FIGS. 6A-6C.

In some exemplary implementations of the trocar insertion systems the exterior of the spring housing (106) can be configured to engage with an aperture (302) of a medical plate (300) such that the spring housing (106) is retained within the aperture (302) and the proximal end of the elongated blade fixture (112) passes through the aperture (302) when a force is applied to the distal end of the elongated blade fixture (112) relative to the medical plate (300). FIGS. 7 and 8 depict one implementation of such a system. FIG. 6A depicts a cut-away view of an implementation of a trocar insertion system when the trocar compression spring (108) is compressed by the force against a medical plate (300), which is not shown in FIG. 6A, and the proximal end (114) of the elongated blade fixture (112) is exposed.

In some exemplary implementations of the trocar insertion systems the exterior of the spring housing (106) comprises a cylinder with a tapered diameter (109) at the proximal end of the elongated blade fixture (112). One such exemplar is depicted in FIG. 10.

The proximal end of the elongated blade fixture can be any shape desired by a user. Suitable shapes can include drivers, screwdrivers, wrenches, cutters, probes, retractors, resectors, awls, prods, or other shapes useful for surgical applications. In some instances of the trocar insertion systems the proximal end of the elongated blade fixture (112) comprises a shape suitable for anchoring into body tissue. In some instances the trocar insertion systems the proximal end of the elongated blade fixture (112) comprises a bone awl. In some instances the trocar insertion systems the proximal end of the elongated blade fixture (112) comprises a shape suitable for forming pilot holes in bone. In some instances the trocar insertion systems the elongated blade fixture (112) further comprises a lumen. In some instances a portion of the elongated blade fixture shaft comprises a cutting or filing zone.

Figure 5A:
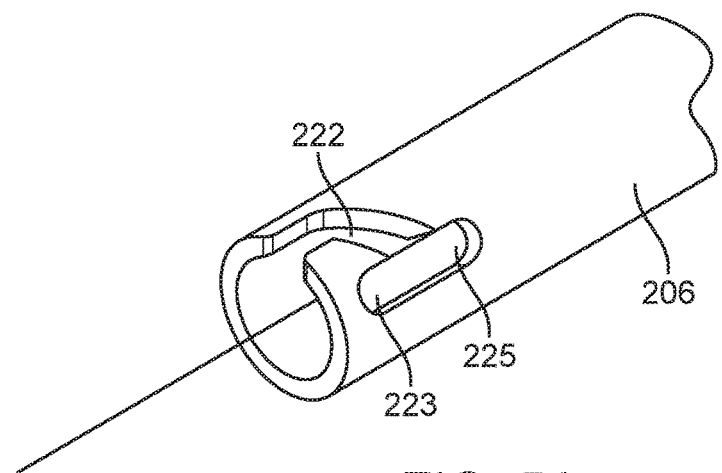
FIGS. 5A-5C illustrates an assembly view of aspects of catches and latches for a trocar device.
Figure 5B:
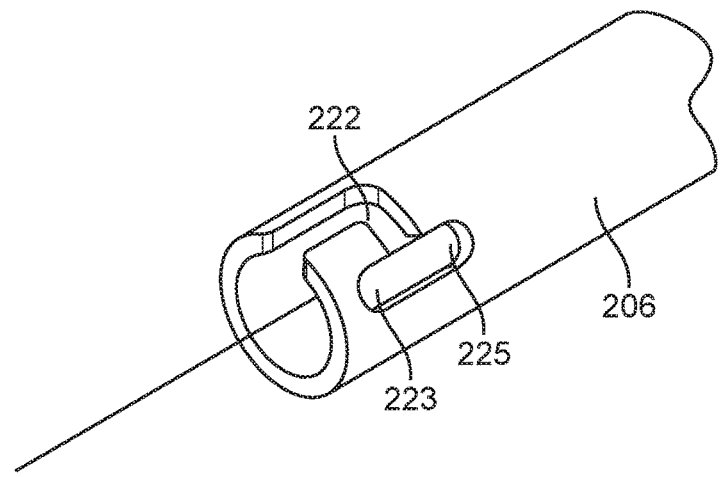
Figure 5C:
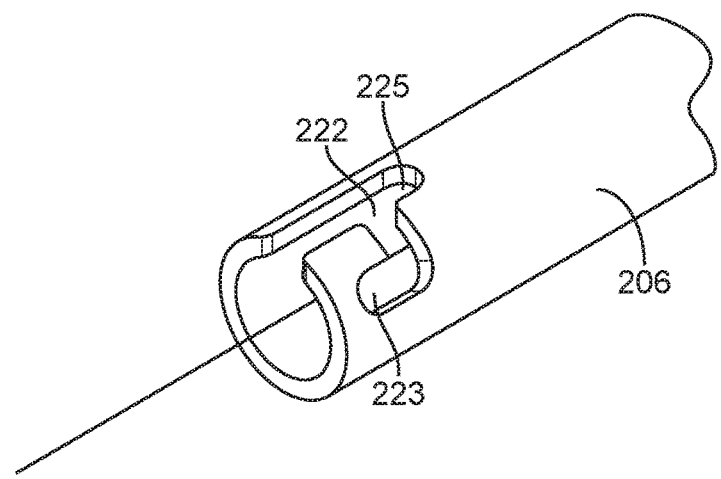

FIGS. 5A-5C depict groove (222) of the driving shaft (206) that is included in some instances of the trocar insertion systems. During detachable engagement, trocar locator pin (124) slides into groove (222) and is held in place in a resting position (223) of the groove by the force exerted by the handle compression spring (224) when the spring is in a compressed state, as depicted in FIGS. 6A and 6B. Groove (222) can be formed in a variety of shapes, provided that the groove (222) allows for insertion of trocar locator pin (124) and provides a resting position (223). In some exemplars, the force applied to the elongated blade fixture (112) during methods of use will compress the handle compression spring (224) such that the trocar locator pin (124) is driven into a working position (225). Working position (225) can be provided in various positions of the groove (222) and preferably allows for the elongated blade fixture (112) to be rotated with the rotation of the driver handle (202) and driving shaft (206). In some exemplars, the force applied to the elongated blade fixture (112) during methods of use will not compress the handle compression spring (224), and the elongated blade fixture (112) can be rotated with the rotation of the driver handle (202) and driving shaft (206) with trocar locator pin (124) remaining in the resting position (223).

The present disclosure also provides kits comprising one or more trocar assemblies (100) and one or more handle assemblies (200). In some exemplary implementations the kits comprise a driver handle (202) with a driving shaft (206) affixed thereto, wherein the driving shaft (206) comprises a first mating feature on the end of the driving shaft (206) opposite the driver handle (202) and one or more trocar assemblies (100). In some instances the one or more trocar assemblies 100 comprise an elongated blade fixture (112) having proximal and distal ends with a second mating feature on the distal end, a spring retention feature (119) located on the elongated blade fixture (112) between the proximal and distal ends, a collar feature (116) located on the elongated blade fixture (112) between the spring retention feature (119) and the distal end, a spring housing cap (110) slidably fitted around the elongated blade fixture (112) between the spring retention feature (119) and the collar feature (116), a trocar compression spring (108) slidably fitted around the elongated blade fixture (112) between proximal end and the spring retention feature (119), a spring housing (106) comprising a hollow body with proximal and distal ends, wherein the distal end is fixedly attached to the spring housing cap (110), wherein the trocar compression spring (108) and spring retention feature (119) are enclosed within the interior volume of the spring housing (106), wherein the trocar compression spring (108) is configured to be compressed between the spring retention feature (119) and a spring catching feature (107) located at the proximal end of the spring housing (106), and wherein at least a portion of the elongated blade fixture (112) is slidably disposed within the spring housing (106) with the central longitudinal axes of the elongated blade fixture (112) and the spring housing (106) being coaxially aligned, and wherein the first mating feature and second mating features are configured for detachable engagement such that the driving shaft (206) and the elongated blade fixture (112) are detachably connected in coaxial alignment. In some instances, kits can further comprise a tool configured for connecting a trocar assembly to the driving shaft (206), detaching a trocar assembly from the driving shaft (206), or both. One exemplar of a kit is depicted in FIG. 9, which can include one or more trocar assemblies 100, one or more handle assemblies 200, one or more fixed drivers 400, one or more torque-limiting drivers 500, one or more medical plates 300, and one or more plate holding forceps 600 contained in a sterile-packed instrument tray 700. In some exemplary implementations, as many of the components in the kits are designed for single-use and are disposable. In some instances, the entire kit is compatible with medical-grade sterilization procedures, including but not limited to ethylene oxide (EtO) and gamma ray sterilization.

The present disclosure also provides devices comprising an elongated blade fixture (112) having proximal and distal ends with a mating feature on the distal end, a spring retention feature (119) located on the elongated blade fixture (112) between the proximal and distal ends, a collar feature (116) located on the elongated blade fixture (112) between the spring retention feature (119) and the distal end, a spring housing cap (110) slidably fitted around the elongated blade fixture (112) between the spring retention feature (119) and the collar feature (116), a trocar compression spring (108) slidably fitted around the elongated blade fixture (112) between proximal end and the spring retention feature (119), and a spring housing (106) comprising a hollow body configured to slidably fit around the elongated blade fixture (112) and attach to the spring housing cap (110). In some instances, the devices may comprise a spring housing (106) that further comprises proximal and distal ends, wherein the distal end is attached to the spring housing cap (110), the trocar compression spring (108) and spring retention feature (119) are enclosed within the interior volume of the spring housing (106), the trocar compression spring (108) is configured to be compressed between the spring retention feature (119) and a spring catching feature (107) located at the proximal end of the spring housing (106), and at least a portion of the elongated blade fixture (112) is slidably disposed within the spring housing (106) with the central longitudinal axes of the elongated blade fixture (112) and the spring housing (106) being coaxially aligned. In some instances the exterior of the spring housing (106) can be configured to engage with an aperture (302) of a medical plate (300) such that the spring housing (106) is retained within the aperture (302) and the proximal end of the elongated blade fixture (112) passes through the aperture (302) when a force is applied to the distal end of the elongated blade fixture (112) relative to the medical plate (300). In some instances of the devices the exterior of the spring housing (106) comprises a cylinder with a tapered diameter (109) at the proximal end of the elongated blade fixture (112). The proximal end of the elongated blade fixture can be any shape desired by a user. Suitable shapes can include drivers, screwdrivers, wrenches, cutters, probes, retractors, resectors, awls, prods, or other shapes useful for surgical applications. In some instances of the devices the proximal end of the elongated blade fixture (112) comprises a shape suitable for anchoring into body tissue. In some instances of the trocar insertion systems the proximal end of the elongated blade fixture (112) comprises a bone awl. In some instances of the devices the proximal end of the elongated blade fixture (112) comprises a shape suitable for forming pilot holes in bone. In some instances of the devices the elongated blade fixture (112) further comprises a lumen. In some instances of the devices a portion of the elongated blade fixture shaft comprises a cutting or filing zone.

The present disclosure provides methods of using one or more trocar assemblies (100) and one or more handle assemblies (200) disclosed herein. In some aspects, the methods of use include methods of fixing medical plates (300) to a body. In other aspects, the methods of use include methods of forming pilot holes in bone tissue. In some exemplary implementations the methods of forming pilot holes in bone tissue can include the use of medical plates (300), and can be used to form pilot holes aligned with apertures (302) of the medical plates (300).

The present disclosure provides methods of fixing a medical plate (300) having one or more apertures (302) to a body, the methods comprising positioning the medical plate (300) adjacent to the body such that at least one of the one or more apertures (302) is oriented towards the body, inserting a first trocar insertion system into a first one of the apertures (302) oriented towards the body, wherein the first trocar insertion system comprises (i) a driver handle (202) with a driving shaft (206) affixed thereto, (ii) a first mating feature on the end of the driving shaft (206) opposite the driver handle (202), (iii) an elongated blade fixture (112) having proximal and distal ends with a second mating feature on the distal end, (iv) a spring retention feature (119) located on the elongated blade fixture (112) between the proximal and distal ends, (v) a collar feature (116) located on the elongated blade fixture (112) between the spring retention feature (119) and the distal end, (vi) a spring housing cap (110) slidably fitted around the elongated blade fixture (112) between the spring retention feature (119) and the collar feature (116), (vi) a trocar compression spring (108) slidably fitted around the elongated blade fixture (112) between proximal end and the spring retention feature (119), and (vii) a spring housing (106) comprising a hollow body with proximal and distal ends, wherein the distal end is fixedly attached to the spring housing cap (110), wherein the trocar compression spring (108) and spring retention feature (119) are enclosed within the interior volume of the spring housing (106), wherein the trocar compression spring (108) is configured to be compressed between the spring retention feature (119) and a spring catching feature (107) located at the proximal end of the spring housing (106), wherein at least a portion of the elongated blade fixture (112) is slidably disposed within the spring housing (106) with the central longitudinal axes of the elongated blade fixture (112) and the spring housing (106) being coaxially aligned, and wherein the first mating feature and second mating feature are detachably engaged such that the driving shaft (206) and the elongated blade fixture (112) are detachably connected in coaxial alignment, the method further comprising engaging the exterior of the first trocar insertion system spring housing (106) with the first aperture (302) oriented towards the body, applying a force to the driver handle (202) relative to the medical plate (300) to move the proximal end of the elongated blade fixture (112) through the first aperture (302) oriented towards the body, fixing the proximal end of the elongated blade fixture (112) to the body, detaching the driving shaft (206) from the elongated blade fixture (112) by disengaging the first mating feature and second mating feature, and removing the driver handle (202) with the driving shaft (206) affixed thereto while leaving the proximal end of the elongated blade fixture (112) fixed to the body. In some exemplary implementations, the methods further comprise positioning the medical plate (300) adjacent to the body such that a second aperture of the one or more apertures (302) is oriented towards the body, and the methods further comprise engaging the first mating feature on the end of the driving shaft (206) with a third mating feature of a trocar device to form a second trocar insertion system, wherein the trocar device comprises (i) an elongated blade fixture (112) having proximal and distal ends with a third mating feature on the distal end, (ii) a spring retention feature (119) located on the elongated blade fixture (112) between the proximal and distal ends, (iii) a collar feature (116) located on the elongated blade fixture (112) between the spring retention feature (119) and the distal end, (iv) a spring housing cap (110) slidably fitted around the elongated blade fixture (112) between the spring retention feature (119) and the collar feature (116), (v) a trocar compression spring (108) slidably fitted around the elongated blade fixture (112) between proximal end and the spring retention feature (119), and (vi) a spring housing (106) comprising a hollow body configured to slidably fit around the elongated blade fixture (112) and attach to the spring housing cap (110), the methods further comprising inserting the second trocar insertion system into the second aperture oriented towards the body, engaging the exterior of the spring housing (106) of the second trocar insertion system with the aperture, applying a force to the driver handle (202) relative to the medical plate (300) to move the proximal end of the elongated blade fixture (112) of the second trocar insertion system through the aperture, fixing the proximal end of the elongated blade fixture (112) of the second trocar insertion system to the body, detaching the driving shaft (206) from the trocar device by disengaging the first mating feature and the third mating feature, and removing the driver handle (202) with the driving shaft (206) affixed thereto while leaving the proximal end of the elongated blade fixture (112) of the trocar device fixed to the body.

The present disclosure provides methods of forming a pilot hole in bone tissue, the methods comprising positioning a medical plate (300) having one or more apertures (302) adjacent to the bone tissue such that at least one of the one or more apertures (302) is oriented towards the bone tissue, inserting a trocar insertion system into one of the apertures (302) oriented towards the body, wherein the trocar insertion system comprises (i) a driver handle (202) with a driving shaft (206) affixed thereto, (ii) a first mating feature on the end of the driving shaft (206) opposite the driver handle (202), (iii) an elongated blade fixture (112) having proximal and distal ends with a second mating feature on the distal end, (iv) a spring retention feature (119) located on the elongated blade fixture (112) between the proximal and distal ends, (v) a collar feature (116) located on the elongated blade fixture (112) between the spring retention feature (119) and the distal end, (vi) a spring housing cap (110) slidably fitted around the elongated blade fixture (112) between the spring retention feature (119) and the collar feature (116), (vii) a trocar compression spring (108) slidably fitted around the elongated blade fixture (112) between proximal end and the spring retention feature (119), and (viii) a spring housing (106) comprising a hollow body with proximal and distal ends, wherein the distal end is fixedly attached to the spring housing cap (110), wherein the trocar compression spring (108) and spring retention feature (119) are enclosed within the interior volume of the spring housing (106), wherein the trocar compression spring (108) is configured to be compressed between the spring retention feature (119) and a spring catching feature (107) located at the proximal end of the spring housing (106), wherein at least a portion of the elongated blade fixture (112) is slidably disposed within the spring housing (106) with the central longitudinal axes of the elongated blade fixture (112) and the spring housing (106) being coaxially aligned, and wherein the first mating feature and second mating feature are detachably engaged such that the driving shaft (206) and the elongated blade fixture (112) are detachably connected in coaxial alignment, the methods further comprising engaging the exterior of the trocar insertion system spring housing (106) with the aperture (302) oriented towards the body, applying a force to the driver handle (202) relative to the medical plate (300) to move the proximal end of the elongated blade fixture (112) through the aperture (302) oriented towards the body, forming the pilot hole in the bone tissue with the proximal end of the elongated blade fixture (112), and removing the trocar insertion system from the medical plate (300) aperture (302).

Those of ordinary skill in the art will appreciate that a variety of materials can be used in the manufacturing of the components in the devices and systems disclosed herein. Any suitable structure and/or material can be used for the various features described herein, and a skilled artisan will be able to select an appropriate structures and materials based on various considerations, including the intended use of the systems disclosed herein, the intended arena within which they will be used, the sterilization parameters and/or sterilants to which they are intended to be exposed, and the equipment and/or accessories with which they are intended to be used, among other considerations. Conventional polymeric, metal-polymer composites, ceramics, and metal materials are suitable for use in the various components. Examples of suitable polymer materials include polyether-imide (Ultem®), polyacrylamide (Ixef®), and other medical grade engineered polymeric (plastic) materials, extruded, injection-molded, or otherwise formed into the desired structures. In some instances, the number of polymer components is maximized in order to provide systems most suitable as single-use disposables. For uses requiring stronger systems, particular components such as the elongated blade fixture (112) and driving shaft (206) can be machined or ground stainless steel, including 302, 316, 416, 420, 440c, 455, 465, 17-4, 17-7, and other grades. In some instances the spring housing (106), trocar locator pin (124), spring stop pin (216), control pin (218), and spring pressure pin (226) can be made from stainless steel, including 302, 316, 416, 420, 440c, 455, 465, 17-4, 17-7, and other grades. Trocar compression spring (108) and handle compression spring (224) can be stainless steel or medical grade engineered polymer, provided they are selected to provide suitable spring rates and cycle life for the desired use. Medical plates (300) can be radiopaque in some instances. Materials hereinafter discovered and/or developed that are determined to be suitable for use in the features and elements described herein would also be considered acceptable.

When ranges are used herein for physical properties, such as molecular weight, or chemical properties, such as chemical formulae, all combinations, and subcombinations of ranges for specific exemplar therein are intended to be included.

The disclosures of each patent, patent application, and publication cited or described in this document are hereby incorporated herein by reference, in its entirety.

Those of ordinary skill in the art will appreciate that numerous changes and modifications can be made to the exemplars of the disclosure and that such changes and modifications can be made without departing from the spirit of the disclosure. It is, therefore, intended that the appended claims cover all such equivalent variations as fall within the true spirit and scope of the disclosure.

What is claimed:

1. A trocar insertion system comprising:
    a driver handle (202) with a driving shaft (206) affixed thereto;
    a first mating feature on a proximal end (220) of the driving shaft (206) opposite the driver handle (202);
    an elongated blade fixture (112) having proximal and distal ends with a second mating feature on the distal end;
    a spring retention feature (119) located on the elongated blade fixture (112) between the proximal and distal ends,
    a collar feature (116) located on the elongated blade fixture (112) between the spring retention feature (119) and the distal end;
    a spring housing cap (110) slidably fitted around the elongated blade fixture (112) between the spring retention feature (119) and the collar feature (116);
    a trocar compression spring (108) slidably fitted around the elongated blade fixture (112) between proximal end and the spring retention feature (119);
    a spring housing (106) comprising a hollow body with proximal and distal ends, wherein
        the distal end is fixedly attached to the spring housing cap (110),
        the trocar compression spring (108) and spring retention feature (119) are enclosed within an interior volume of the spring housing (106),
        the trocar compression spring (108) is configured to be compressed between the spring retention feature (119) and a spring catching feature (107) located at the proximal end of the spring housing (106), and, at least a portion of the elongated blade fixture (112) is slidably disposed within the spring housing (106) with central longitudinal axes of the elongated blade fixture (112) and the spring housing (106) being coaxially aligned;

wherein the first mating feature and second mating feature are detachably engaged such that the driving shaft (206) and the elongated blade fixture (112) are detachably connected in coaxial alignment;

wherein:

the driving shaft (206) comprises a hollow tube;

the driving shaft (206) further comprises:
- a first aperture and a second aperture through walls of the hollow tube on opposite sides of a central longitudinal axis of the hollow tube,
- a third aperture through the wall of the hollow tube in a position between a location of the first and second apertures and a proximal end of the hollow tube, and,
- a groove (222) through the wall of the hollow tube at the proximal end;

the trocar insertion system further comprises:
- a spring stop pin fixed within the first and second apertures and passing through the central longitudinal axis of the hollow tube;
- a control pin fixed within the third aperture and partially extending into an interior volume of the hollow tube;
- a spring pressure pin (226) comprising a cylinder configured to slide within the interior volume of the hollow tube, positioned within the interior volume of the hollow tube with a longitudinal axis of the cylinder aligned with the hollow tube longitudinal axis,
    - wherein the spring pressure pin (226) has a reduced diameter in a portion of the middle of side walls,
    - wherein the reduction in diameter is at least as large as a portion of the control pin that partially extends into the interior volume of the hollow tube,
    - and wherein the spring pressure pin (226) is positioned such that the portion of the control pin that partially extends into the interior volume of the hollow tube is slidably contained within the volume of the reduced diameter portion of the spring pressure pin (226) between two non-reduced-diameter end regions of the spring pressure pin (226), and,
- a handle compression spring (224) positioned within an interior volume of the hollow tube between the spring stop pin and the spring pressure pin (226);
- a fourth aperture located on the elongated blade fixture (112) between the collar feature (116) and the distal end, and the distal end of the elongated blade fixture (112) is configured to slidably fit within the interior of the proximal end of the hollow tube;
- a trocar locator pin fixed within the fourth aperture and partially extending outward from a surface of the elongated blade fixture (112);

the driving shaft (206) and elongated blade fixture (112) are detachably connected by a detachable engagement of the trocar locator pin within the groove (222) of the driving shaft (206); and, the handle compression spring (224) is at least partially compressed by the spring pressure pin (226), which is slidably contained between the distal end of the elongated blade fixture (112) and the handle compression spring (224).

2. The trocar insertion system according to claim 1, wherein the first mating feature and second mating feature comprise a pair of helical threads that can detachably engage together.

3. The trocar insertion system according to claim 1, wherein the first and second mating features comprise a ball detent mechanism arrangement wherein one of the driving shaft (206) and elongated blade fixture (112) can be received within the other such that a spring-loaded ball falls partially into an aperture in order to detachably connect the driving shaft (206) and elongated blade fixture (112).

4. The trocar insertion system according to claim 1, wherein the second mating feature comprises a protruding part and the first mating feature comprises a depression adapted to receive the protruding part in a snap joint configuration.

5. The trocar insertion system according to claim 1, wherein an exterior of the spring housing (106) is configured to engage with an aperture (302) of a medical plate (300) such that the spring housing (106) is retained within the aperture (302) and the proximal end of the elongated blade fixture (112) passes through the aperture (302) when a force is applied to the distal end of the elongated blade fixture (112) relative to the medical plate (300).

6. The trocar insertion system according to claim 1, wherein an exterior of the spring housing (106) comprises a cylinder with a tapered diameter at the proximal end of the elongated blade fixture (112).

7. The trocar insertion system according to claim 1, wherein the proximal end of the elongated blade fixture (112) comprises a shape suitable for anchoring into body tissue.

8. The trocar insertion system according to claim 1, wherein the proximal end of the elongated blade fixture (112) comprises a bone awl.

9. The trocar insertion system according to claim 1, wherein the proximal end of the elongated blade fixture (112) comprises a shape suitable for forming pilot holes in bone.

10. A device comprising:
- an elongated blade fixture (112) having proximal and distal ends with a mating feature on the distal end;
- a spring retention feature (119) located on the elongated blade fixture (112) between the proximal and distal ends;
- a collar feature (116) located on the elongated blade fixture (112) between the spring retention feature (119) and the distal end;
- a spring housing cap (110) slidably fitted around the elongated blade fixture (112) between the spring retention feature (119) and the collar feature (116);
- a trocar compression spring (108) slidably fitted around the elongated blade fixture (112) between proximal end and the spring retention feature (119);
- a spring housing (106) comprising a hollow body configured to slidably fit around the elongated blade fixture (112) and attach to the spring housing cap (110); and,
- wherein the elongated blade fixture further comprises a lumen.

11. The device of claim 10, wherein:

the spring housing (106) further comprises proximal and distal ends, wherein:

the distal end is attached to the spring housing cap (110), the trocar compression spring (108) and spring retention feature (119) are enclosed within an interior volume of the spring housing (106), the trocar compression spring (108) is configured to be compressed between the spring retention feature (119) and a spring catching feature (107) located at the proximal end of the spring housing (106), and, at least a portion of the elongated blade fixture (112) is slidably disposed within the spring housing (106) with central longitudinal axes of the elongated blade fixture (112) and the spring housing (106) being coaxially aligned.

12. The device according to claim 10, wherein an exterior of the spring housing (106) is configured to engage with an aperture (302) of a medical plate (300) such that the spring housing (106) is retained within the aperture (302) and the proximal end of the elongated blade fixture (112) passes through the aperture (302) when a force is applied to the distal end of the elongated blade fixture (112) relative to the medical plate (300).

13. The device according to claim 10, wherein an exterior of the spring housing (106) comprises a cylinder with a tapered diameter at the proximal end of the elongated blade fixture (112).

14. The device according to claim 10, wherein the proximal end of the elongated blade fixture (112) comprises a shape suitable for anchoring into body tissue.

15. The device according to claim 10, wherein the proximal end of the elongated blade fixture (112) comprises a bone awl.

16. The device according to claim 10, wherein the proximal end of the elongated blade fixture (112) comprises a shape suitable for forming pilot holes in bone.

* * * * *